(12) United States Patent
Love et al.

(10) Patent No.: US 9,244,071 B2
(45) Date of Patent: Jan. 26, 2016

(54) COMPOSITIONS AND METHODS FOR ASSESSING CYTOTOXICITY OF SINGLE CELLS

(75) Inventors: J. Christopher Love, Somerville, MA (US); Bruce Walker, Nahant, MA (US); Navin Varadarajan, Somerville, MA (US); Boris Julg, Boston, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 631 days.

(21) Appl. No.: 13/145,300

(22) PCT Filed: Jul. 13, 2009

(86) PCT No.: PCT/US2009/050411
§ 371 (c)(1),
(2), (4) Date: Oct. 11, 2011

(87) PCT Pub. No.: WO2010/085275
PCT Pub. Date: Jul. 29, 2010

(65) Prior Publication Data
US 2012/0149592 A1 Jun. 14, 2012

Related U.S. Application Data

(60) Provisional application No. 61/146,106, filed on Jan. 21, 2009.

(51) Int. Cl.
*C40B 30/06* (2006.01)
*G01N 33/569* (2006.01)
*G01N 33/50* (2006.01)

(52) U.S. Cl.
CPC ...... *G01N 33/56972* (2013.01); *G01N 33/5047* (2013.01); *C40B 30/06* (2013.01); *G01N 2333/16* (2013.01)

(58) Field of Classification Search
None
See application file for complete search history.

(56) References Cited

U.S. PATENT DOCUMENTS

| | | | |
|---|---|---|---|
| 4,729,949 A | 3/1988 | Weinreb et al. |
| 6,210,910 B1 | 4/2001 | Walt et al. |
| 6,377,721 B1 | 4/2002 | Walt et al. |
| 6,410,252 B1 | 6/2002 | Lehmann et al. |
| 7,776,553 B2 | 8/2010 | Love et al. |
| 2002/0142351 A1 | 10/2002 | Diamond |
| 2010/0216228 A1 | 8/2010 | Love et al. |
| 2011/0111981 A1 | 5/2011 | Love et al. |
| 2011/0124520 A1 | 5/2011 | Love et al. |

(Continued)

FOREIGN PATENT DOCUMENTS

| | | |
|---|---|---|
| WO | WO-02/078844 A1 | 10/2002 |
| WO | WO-2007035633 A2 | 3/2007 |

OTHER PUBLICATIONS

International Search Report of PCT/US09/50411, 2 pages (mailed Mar. 12, 2010).

(Continued)

*Primary Examiner* — Christian Boesen
(74) *Attorney, Agent, or Firm* — Choate, Hall & Stewart, LLP

(57) ABSTRACT

The invention provides a method of analyzing interactions between pairs of target and effector cells utilizing high-throughput screenings methods for profiling large numbers of single cells in microarrays.

19 Claims, 7 Drawing Sheets

(56) References Cited

U.S. PATENT DOCUMENTS

| | | |
|---|---|---|
| 2011/0281764 A1 | 11/2011 | Love et al. |
| 2012/0015824 A1 | 1/2012 | Love et al. |
| 2012/0149592 A1 | 6/2012 | Love et al. |

OTHER PUBLICATIONS

Written Opinion of PCT/US09/50411, 3 pages (mailed Mar. 12, 2010).

Bradshaw et al., Concurrent Detection of Secreted Products from Human Lymphocytes by Microengraving: Cytokines and Antigenreactice Antibodies, Clinical Immunology, 2008, 129(1): 10-18.

Saez-Cirion et al., HIV Controllers Exhibit Potent CD8 T cell capacity to suppress HIV Infection Ex Vivo and Peculiar Cytotoxic T Lymphocyte Activation Phenotype, Proceedings of the National Academy of Sciences, 2007, 104(16): 6776-6781.

Snyder et al., Measuring the Frequency fo Mouse and Human Cytoxic T cells by the Lysispot Assay: Independent Regulation of Cytokine Secretion and Short-Term Killing, Nature Medicine, 2003, 9(2): 231-236.

Extended European Search Report for 09839012.3, dated Sep. 4, 2012, 9 pages.

Abbas, et al., Cellular and Molecular Immunology, 2nd Ed.: 92-93 (1994).

Alter, G. et al., Differential natural killer cell-mediated inhibition of HIV-1 replication based on distinct KIR/HLA subtypes, The Journal of Experimental Medicine, 204(12):3027-3036 (2007).

Alter, G. et al., Evolution of Innate and Adaptive Effector Cell Functions during Acute HIV-1 Infection, J. Infect. Dis. 195:452-1460 (2007).

Altfeld, M. et al., HLA Alleles Associated with Delayed Progression to Aids Contribute Strongly to the Initial CD8+ T Cell Response Against HIV-1, PLoS. Med., 3(10):1851 (2006).

Appay, V. et al., HIV specific CD8+ T Cells Produce Antiviral Cytokines but Are Impaired in Cytolytic Function, J. Exp. Med. 192(1):63-75 (2000).

Barouch, D. H., Challenges in the development of an HIV-1 vaccine, Nature, 455:613-619 (2008).

Chen, H.J.H. et al., A Novel Micro-Well Array Chip for Liquid Phase Biomaterial Processing and Detection, Sensors and Actuators, 108:193-200 (2003).

Clark et al., Regulation of Human B-Cell Activation and Adhesion, Annual Review Immunology, 9: 97-127 (1991).

Cooper, M.A. et al., The biology of human natural killer-cell subsets, Trends in Immunol. 22(11):633-640 (2001).

Deeks, S. G. and Walker, B. D. Human Immunodeficiency Virus Controllers: Mechanisms of Durable Virus Control in the Absence of Antiretroviral Therapy, Immunity, 27:406-416 (2007).

Extended European Search Report for EP 09839012.3, 9 pages (Sep. 4, 2012).

Faroudi, M. et al., Lytic versus stimulatory synapse in cytotoxic T lymphocyte/target cell interaction: Manifestation of a dual activation threshold, Proc. Natl. Acad. Sci., 100(24):14145-14150 (2003).

Fauci, A. S. et al., Perspective-HIV Vaccine Research: The Way Forward, Science, 321:530-532 (2005).

Fogli, M. et al., Lysis of Endogenously Infected CD4+ T Cell Blasts by rIL-2 Activated Autologous Natural Killer Cells from HIV-Infected Viremic Individuals, Plos Pathogens 4(7):1-13 (2008).

Hecht, F M. et al., Use of laboratory tests and clinical symptoms for identification of primary HIV infection, AIDS, 16:1119 (2002).

International Preliminary Report on Patentability for PCT/US2009/050411, 4 pages (Jul. 26, 2011).

Kahn, J. O. and Walker, B. D., Acute Human Immunodeficiency Virus Type I Infection, N. Engl. J. Med. 339(1):33 (1995).

Kim, H. et al., Live Lymphocyte Arrays for Biosensing, Adv. Funct. Mater., 16:1313 (2006).

Koefoed, K. et al., Molecular characterization of the circulating anti-HIV-1 gp120-specific B cell repertoire using antibody phage display libraries generated from preselected HIV-1 gp120 binding PBLs, J. Immunol. Methods, 297:187-201 (2005).

Koff, W. C. et al., HIV vaccine design: insights from live attenuated SIV vaccines, Nature Immunology, 7(1):19-23 (2006).

Liu, L. et al., Visualization and quantification of T cell-mediated cytotoxicity using cell-permeable fluorogenic caspase substrates, Nature Medicine 8(2):185 (2002).

Long, B. R. et al., Conferral of Enhanced Natural Killer Cell Function by KIR3DS1 in Early Human Innnunodeficiency Virus Type 1 Infection, Journal of Virology, 82(10):4785-4792 (2008).

Love, J. C. et al., A microengraving method for rapid selection of single cells producing antigen-specific antibodies, Nature Biotechnology, 24(6):703 (2006).

Mangasarian, A. et al., Nef-Induced CD4 and Major Histocompatibility Complex Class I (MHC-I) Down-Regulation Are Governed by Distinct Determinants: N-Terminal Alpha Helix and Proline Repeat of Nef Selectively Regulate MHC-I Trafficking, Journal of Virology, 73(3):1964 (1999).

Martin, M. P. et al., Innate partnership of HLA-B and KIR3DL1 subtypes against HIV-1, Nature Genetics, 39(6):733-740 (2007).

Migueles, S. A. et al., HIV-specific CD8+ T cell proliferation is coupled to perforin expression and is maintained in nonprogressors, Nature Immunology, 3(11):1061 (2002).

Moretta, A. et al., What is a natural killer cell? Nature Immunology, 3(1):6-8 (2002).

Muraguchi et al., Method for Cloning Antigen-Specific Lymphocyte Antigen Receptor Gene, English Translation of Japanese Patent Application No. 2002-346728, (filed Nov. 29, 2002).

Muraguchi et al., Microwell Array Chip for Detecting Antigen-Specific Lymphocytes and Method for Detecting Antigen-Specific Lymphocytes, English Translation of Japanese Patent Application No. 2002-331031, (filed Nov. 14, 2002).

Ostuni, E. et al., Selective Deposition of Proteins and Cells in Arrays of Microwells, Langmuir, 17:2828-2834 (2001).

Pulendran, B. and Ahmed, R., Translating Innate Immunity Into Immunological Memory: Implications for Vaccine Development, Cell, 124:849-863 (2006).

Ronan, J. L. et al., Optimization of the surfaces used to capture antibodies from single hybridomas reduces the time required for microengraving, Journal of Immunological Methods, 340:164-169 (2009).

Shaykhiev et al., Interactions Between Epithelial Cells and Leukocytes in Immunity and Tissue Homeostasis, Journal of Leukocyte Biology, 82(1): 1-15 (2007).

Steenbakkers, P. G. et al., A new approach to the generation of human or murine antibody producing hybridomas, Journal of Immunological Methods, 152:(1)69-77 (1992).

Story, C. M. et al., Profiling antibody responses by multiparametric analysis of single B cells, PNAS, 105(46):17902-17907 (2008).

Stratov, I. et al., Robust NK Cell-Mediated Human Immunodeficiency Virus (HIV)-Specific Antibody-Dependent Responses in HIV-Infected Subjects, Journal of Virology, 82:5450-5459 (2008).

Valiutti, S. et al., Different Responses are Elicited in Cytotoxic T Lymphocytes by Different Levels of T cell Receptor Occupancy, J. Exp. Med., 183:1917 (1996).

Varadarajan, N. et al., A high-throughput single-cell analysis of human CD8+ T cell functions reveals discordance for cytokine secretion and cytolysis, Journal of Clinical Investigation, 121(11):4322-4331 (2011).

Walker, B. D. and Burton, D. R., Toward an AIDS Vaccine, Science, 320:760-764 (2008).

Wang, X. W. and Stollar, B. D., Human immunoglobulin variable region gene analysis by single cell RT-PCR, Journal of Immunological Methods, 244:217-225 (2000).

Yamamura et al., "Single-cell microarray for analyzing cellular response", *Analytical Chemistry*, 77(24): 8050-8056 (2005).

SEQUENCE LISTING

<160> NUMBER OF SEQ ID NOS: 5

<210> SEQ ID NO 1

-continued

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Ala Arg Ile Gly His Arg Phe Leu Glu Trp Tyr Leu Asn Asp Tyr
1               5                   10                  15

Trp

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Ala Arg Asp Met Gly Cys Gly Gly Asp Cys Tyr His Asp Ala Phe
1               5                   10                  15

Asp Ile Trp

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Ala Arg Glu Ala Thr Ala Met Ala Ala Tyr Phe Asp Tyr Trp
1               5                   10                  15

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Ala Lys Thr Thr Val Thr Ile Thr Leu Asn Tyr Gly Met Asp Val
1               5                   10                  15

Trp

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any amino acid

<400> SEQUENCE: 5

Cys Ala His Arg Gly Gln Asp Thr Phe Xaa Tyr Trp
1               5                   10
```

COMPOSITIONS AND METHODS FOR ASSESSING CYTOTOXICITY OF SINGLE CELLS

RELATED APPLICATIONS

This application is a national stage application, filed under 35 U.S.C. §371, of International Application No. PCT/US2009/050411, filed Jul. 13, 2009, which claims the benefit of provisional application, U.S. Ser. No. 61/146,106, filed Jan. 21, 2009, the contents of which are herein incorporated by reference in their entirety.

SEQUENCE LISTING

The instant application contains a Sequence Listing which has been submitted electronically in ASCII format and is hereby incorporated by reference in its entirety. Said ASCII copy, created on Dec. 31, 2013, is named 0492611-1117_SL.txt and is 1,917 bytes in size.

FIELD OF THE INVENTION

The invention provides a method of analyzing interactions between pairs of target and effector cells utilizing high-throughput screenings methods for profiling large numbers of single cells in microarrays.

BACKGROUND OF THE INVENTION

Despite more than twenty five years of research on the interactions between humans and the human immunodeficiency virus type 1 (HIV-1), HIV/AIDS remains one of the most prevalent threats to global health. Current estimates suggest it will become the third leading cause of mortality worldwide over the next twenty years behind cancer and cardiovascular disease. A vaccine that would either prevent infection or elicit natural mechanisms to control the disease has not yet been developed. Existing analytical tools simply are not adequate to define the critical characteristics associated with cells of the immune system that provide effective protective immunity to the virus. Technologies such as flow cytometry and immunosorbant assays (ELISpot, ELISA) can evaluate populations of cells, but have poor sensitivity for rare events. Other important functions, such as cytotoxicity and proliferation, can only be measured in bulk presently. Together, these limitations make it difficult, if not impossible, to evaluate the human immune response to HIV with sufficient clarity to determine correlates of protection. As such, there is a pressing need for new strategies for analyzing protective immunity to viruses such as HIV.

SUMMARY OF THE INVENTION

The invention provides methods for identifying CD8+ cells able to lyse CD4+ HIV-infected cells in a subject by providing a suspension of effector CD8+ cells and target cells from a subject deposited onto a moldable slab containing at least one microwell in a microwell array, wherein at least one microwell in the microwell array has a single effector cell; culturing the suspension under conditions allowing for lysis of the target cell by the CD8+ cells; detecting lysis of the target cell by the effector cells, and identifying CD8+ cells able to lyse CD4+ HIV-infected cells. Optionally, the effector cells that lyse the target cell are recovered. Preferably, the recovered effector cells that have lysed the target cell are cultured. In one aspect, the effector cells and target cells are mixed prior to depositing cells into the microwell. Alternatively, the effector cells and target cells are mixed after depositing cells into the microwell. Lysis is detected by monitoring change in fluourscence of a labeled cell. Alternatively, lysis is detected by monitoring changes in intracellular calcium levels of the target cell. The calcium is detected with a calcium sensitive fluorescent dye. Preferably, the calcium sensitive fluorescent dye is Fura 2AM (Invitrogen).

In one aspect, the microwell array is contacted with a substrate, wherein the substrate is pretreated with at least one agent that specifically detects a product of the effector cell, followed by detection of the agent. The agent is an antibody, cytokine, or soluble mediator of lysis. Preferably, the cytokine is TNF-α or IFN-γ. Optionally, the soluble mediator of lysis is granzyme B (GzB) or perforin. The method of the invention optionally further comprises labeling an effector cell with CD69.

The invention also provides for methods of characterizing an antibody response in a subject by providing a suspension of B cells from a subject deposited onto a moldable slab containing at least one microwell in a microwell array, wherein the subject is infected with or suspected of being infected with HIV, and wherein at least one microwell in the microwell array contains a single cell; contacting the microwell array with a substrate, wherein the substrate is pretreated with at least one B cell detection agent; and detecting the agent, thereby characterizing the antibody response. Preferably, the B cell detection agent is an antibody specific for an epitope in gp120.

In one aspect, the method of the invention further comprises contacting the microwell array with a second substrate, wherein the substrate is pretreated with at least one first B cell detection agent. Optionally, the first B cell detection agent is an antibody for HIV gp120. Preferably, the antibody is to the C-terminus of HIV gp120. In one aspect, the isotype of antibody produced by the B cell in the microwell array is determined. The B cell expressing an antibody reactive with HIV is optionally isolated. In another aspect, the light chain and heavy chain variable regions of the antibody are isolated and amplified. The B cells are optionally exposed to an agent that stimulated production of antibodies in the cell. Preferably, the agent is CD40L or an anti-BCR antibody. In another aspect, the B cells are exposed to CD40L and an anti-BCR antibody.

The invention also provides methods for characterizing cross-reactivity of a B cell to multiple HIV isolates by providing a suspension of B cells from a subject deposited onto a moldable slab containing at least one microwell in a microwell array, wherein the subject is infected with or suspected of being infected with HIV, and wherein at least one microwell in the microwell array has a single cell; contacting the microwell array with a first substrate, wherein the substrate is pretreated with antibodies produced by the B cells in the at least one microwell; contacting the substrate with a first labeled HIV virion and a second labeled HIV virion; and determining whether the first labeled virion and second labeled virion bind to antibodies produced by the same cell in the microwell. Optionally, the B cells producing antibodies that bind specifically to the first labeled virion and second labeled virion are recovered. In one aspect, the recovered B cells are cultured. Preferably, at least one of the virions are labeled. Alternatively, the first virion and second virion are distinctly labeled, i.e., labeled with a different detectable marker.

The invention also provides methods of generating a functional profile for an effector cell responsive to an HIV infection in a subject, by providing a population of effector cells selected from the group consisting of a CTL (CD8+), NK cells}

(CD16$^+$), NK T cells (CD1d$^+$,Vα24$^+$), or γδ T cells (Vγ9$^+$, Vγ2$^+$), wherein the effector cells are obtained from a subject deposited onto a moldable slab containing at least one microwell in a microwell array, wherein at least one microwell in the microwell array has a single effector cell, wherein the population of effector cells is co-loaded with a cognate target cell population; visualizing the effector cells; assessing cytotoxicity of the effector cells; contacting the microwell array with a first substrate, wherein the substrate is pretreated with an agent that specifically detects one of more of IL-2, IL-4, IL-10, TNF-α, and IFN-γ; and determining whether the effector cells in the microwell binds the one or more agents. In one aspect, the cytotoxicity is assessed by detecting release of Calcein AM. Optionally, the cells are labeled for one or more specific surface marker proteins. Preferably, the surface marker protein is CD62L, CXCR3, CCR4, or CCR7. In another aspect, an effector cell is recovered from one or more microwell. Optionally, the recovered cell is cultured to obtain a clonal amplification of the recovered cell. The expression of one or more genes in the recovered cell is optionally characterized. The recovered cell is preferably CD8$^+$ cytotoxic T cells (CTL), natural killer (NK) cells, NK T cells, or γδ T cells. In another aspect, the subject is at an acute stage of infection, a highly active antiretroviral therapy (HAART) subject, or an elite controller.

The invention also provides methods of assessing an innate immune response in a subject with an HIV infection, by providing a suspension of NK cells from a subject deposited onto a moldable slab containing at least one microwell in a microwell array, wherein the subject is infected with or suspected of being infected with HIV, and wherein at least one microwell in the microwell array has a single cell deposited; and contacting the microwell array with a substrate, wherein the substrate is pretreated with at least one NK cell detection agent; and detecting the agent, thereby detecting NK cells and assessing the innate immune response. In one aspect, the NK cells are detected using NKp46-Cy3, CD107a-Alexa647, and/or CD69-Alexa488. The NK cell detection agent detects NK cells. The cells are optionally co-cultured prior to depositing onto the moldable slab. Preferably, the cells are co-cultured with IL-12 and IL-18.

The invention also provides methods of assessing clonal diversity in a population of NK cells by providing a suspension of NK cells and target cells from a subject deposited onto a moldable slab containing at least one microwell in a microwell array, wherein at least one microwell in the microwell array has a single effector cell; culturing the suspension under conditions allowing for lysis of the target cell by the NK cells; detecting lysis of the target cell by the effector cells; and identifying the effector cells, thereby assessing clonal diversity in the population of NK cells. In one aspect, the effector cells that lyse the target cell are recovered and optionally cultured. In another aspect, the NK cells that have lysed the target cell are recovered. Optionally, the NK cells and target cells are mixed prior to depositing cells into the microwell. Alternatively, the NK cells and target cells are mixed after depositing cells into the microwell. In one aspect, lysis of target cells is determined by monitoring a change in fluorescence of a labeled cell. In yet another aspect, the NK cell that has lysed a target cell is isolated and a killer cell immunoglobulin-like receptor (KIR) gene on the NK cell is detected. The microwell array is optionally contacted with a substrate, wherein the substrate is pretreated with at least one agent that can specifically detect a product of the NK cell; and detecting the agent. The agent is an antibody, cytokine, or soluble mediator of lysis. Preferably, the cytokine is TNF-α or IFN-γ.

The invention also provides methods of assessing diversity in a population of NK and B cells by providing a suspension of cells comprising expanded HIV-infected CD4+ cells T cell, activated NK cells, and B cells and target cells, wherein the suspension is deposited onto a moldable slab containing at least one microwell in a microwell array, wherein at least one microwell in the microwell array has a single T cell; culturing cells under conditions that allow antibodies produced by B cells to bind to surface of T cells; identifying wells containing a B cell, a NK cell, and a lysed T cell, and identifying B cell or NK cell. In one aspect, the NK cells are activated with IL-2. In another aspect, the B cells are activated with CD40L or anti-BCR. In yet another aspect, the B cells are activated with CD40L and anti-BCR antibody. The NK cells are activated with IL-2. The B cells are activated with CD40L of an anti-BCR antibody. Optionally, the B cells or NK cells are recovered from the well; and one or more properties of the B cells are characterized. In another aspect, antibody genes in the B cells are characterized. The VDJ region of genes encoding antibodies in the B cells is optionally analyzed. The microwell array is optionally contacted with a substrate under conditions that allow antibodies produced by the B cells to attach to the substrate. In another aspect, the substrate is contacted with lysates from an HIV infected cell and wells with B cells producing antibodies that bind to the HIV lysate or anti-IgG3 antibody are identified. Preferably, wells with B cells producing antibodies that bind to the HIV lysate or anti-IgG3 antibody are identified.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

Figure 1:
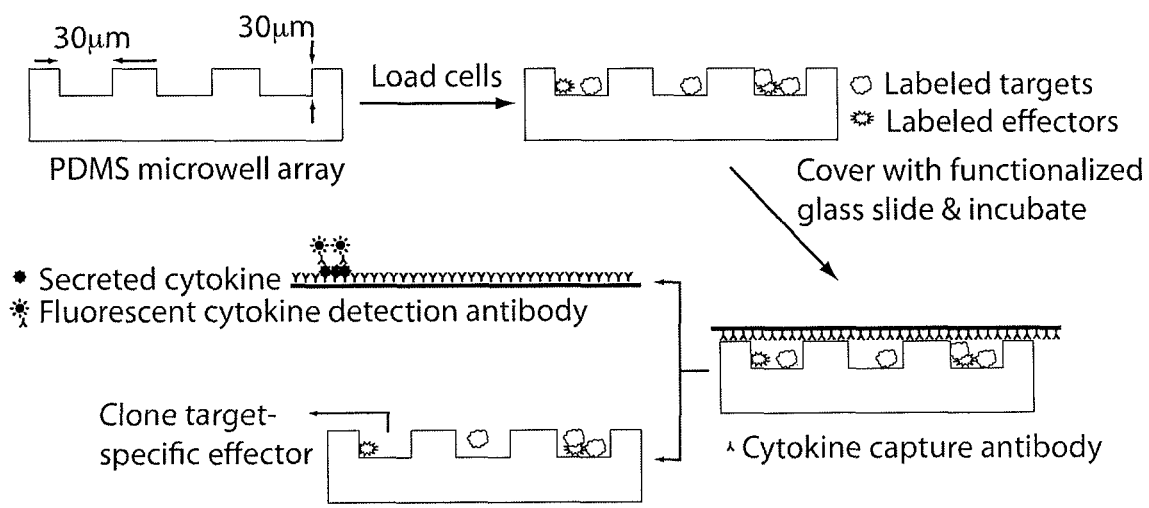
FIG. 1 is an illustration of an assay scheme. The cells, fluorescently labeled targets (stained with Calcein, green) and effectors (stained with α-CD8 APC, pink), are loaded onto ~30 μm microwell array and imaged on a fluorescent microscope. The microwell array is then covered with a glass-slide pre-functionalized with capture antibodies and incubated at 37° C., 5% CO$_2$ for 2-6 h. Post-incubation, secreted cytokines are detected on the glass side using specific fluorescent antibodies and targets lysed by specific effectors are imaged by their loss of fluorescence (well 1). In microwells that contain only target cells (well 2) and in microwells that contain effectors incapable of lysing the target (well 3) there should be very little change in fluorescence of the target.

A thorough knowledge of the mechanisms employed by human immunodeficiency virus (HIV) to evade the immune system is essential to design effective vaccines and therapies. The progression of disease for untreated individuals is marked by the persistence of viral replication and the loss of CD4+ T cells (Kahn J O, Walker B D (1998) Acute human immunodeficiency virus type I infection. *N. Engl. J. Med.* 339, 33; Hecht F M et al. (2002) Use of laboratory tests and clinical symptoms for identification of primary HIV infection. *AIDS* 16, 1119). Virus-specific CTLs play a significant role in controlling persistent replication and the initial appearance of HIV-1 specific CD8+ T cells has shown to decrease viral loads (Altfeld M et al. (2006) HLA Alleles Associated with delayed progression to AIDS contribute strongly to the initial CD8+ T cell response against HIV-1 *PLoS. Med.* 3(10), 1851). This decrease in viral replication, however, is transient in most individuals (progessors). A very small subset of individuals designated as LTNPs (elite controllers) maintain low viral thresholds over extended periods of time and the virus specific CD8+ T cells identified in these individuals have been shown to have greater proliferative capacity compared to the same cells isolated from progressors (Migueles S A et al. (2002) HIV-specific CD8+ T cell proliferation is coupled to perforin expression and is maintained in nonprogressors *Nat. Immun.* 3(11), 1061).

Prior to the invention described herein, there were two challenges inherent to studying the interactions between a pathogen and the human immune system: 1) the number of cells available in most clinical samples is often very limited; and 2) unique clones, such as pathogen-specific B cells or T cells, are rare. Existing analytical tools also are not sufficient to assign multiple characteristics (lineage, function, genotype) simultaneously to the same individual cell. For example, flow cytometry is a common technique used to evaluate populations of single cells for surface-expressed phenotypic markers, but analysis of cytokine profiles, which indicate certain functional phenotypes, requires fixing and permeabilizing the cells. This loss of viability means that additional functional characteristics such as cytotoxicity cannot be assessed directly, and genetic analysis is also often hindered. Thus, prior to the invention described herein, it was not possible to resolve unambiguously the fine heterogeneity in the subsets of cells from the innate and adaptive immune systems that are responding to a particular infectious agent. It was also difficult to build a comprehensive snapshot of the state of the immune system. Such profiles improve the identification of the mechanisms that confer protection against certain pathogens and diagnostic indicators for healthy responses. Therefore, the invention provides new technologies for measuring and correlating lineages, functions, and genotypes to many individual cells to enhance studies on the interactions between the human immune system and pathogens of interest, especially for HIV (Fauci, A. S., Johnston, M. I., Dieffenbach, C. W., Burton, D. R., Hammer, S. M., Hoxie, J. A., Martin, M., Overbaugh, J., Watkins, D. I., Mahmoud, A. & Greene, W. C. Perspective—HIV vaccine research: The way forward. *Science* 321, 530-532 (2008)).

The invention provides methods and compositions for characterizing a subject's immune response to an infection, including infection by human immunodeficiency virus. Microarrays and slabs can be constructed using methods known in the art, including those described in PCT/US2006/036282 (published as WO/2007/035633) and U.S. Ser. No. 61/057,371. The contents of both of these applications are incorporated herein by reference in their entirety. As used herein, "moldable slab" refers to an apparatus which can flex, move or distort, at least in one dimension, when placed in contact with a substrate. For example, in certain configurations the moldable slab may include a material, e.g., an elastomeric material, such that as the moldable slab is placed in contact with a substrate, a substantially fluid tight seal is formed between the moldable slab and the substrate to retard or to prevent any fluid in the moldable slab from escaping or leaking.

Antiviral Cytotoxic T-Lymphocyte (CTL) Function in HIV Inhibition

Cytotoxic CD8+ T-cells (CTL) play a pivotal role in the clearance of acute viral infections and the control of persistent virus reservoirs. Depletion of CD8+ lymphocytes in macaques infected with SIV results in a rapid and marked increase in viremia. Nevertheless, chronic HIV-1 infection is associated with abundant quantities of HIV-specific CD8+ T cells, in the absence of viral clearance or control. These data suggest that the functions, not just the numbers, of CD8+ T cells are critical for effectively controlling viral replication.

To date, the potency of HIV-specific CD8+ T-cell activity has been determined either by assessing the frequency of HIV-specific CD8+ T cells by labeling cells with tetramers of peptide-HLA class I complexes, or by the ability of these T cells to secrete IFN-γ upon antigenic stimulation. Recent studies, however, show that the frequency and secretion of IFN-γ by CD8+ T cells do not correlate with the control of viremia in chronic HIV-1 infection.

The ability of CTLs to suppress HIV replication is measured by co-culturing HIV-infected CD4+ T-cells and autologous bulk CD8+ T-cells. These experiments show heterogeneous results for the ability of individuals to inhibit HIV. Recent results suggest that ex vivo CD8+ T cell responses do not correlate with the capacity of these cells to inhibit HIV-1 replication in vitro. Rather it is the CD8+ T cells that are able to proliferate in sufficient amounts to fight the virus that are able to gain control over the virus, but the phenotype, functional attributes, and genetic transcriptional profile (maturation/exhaustion) of these cells are not known.

Although the importance of virus-specific CD8+ T cells in controlling disease progression seems clear, their characterization and isolation has been challenging. A variety of methods, each with its own merits and disadvantages, have been used to isolate these CTLs. Limiting dilution assay can be used isolate antigen-specific clones, but is dependent on the ability of these clones to multiply in tissue culture. ELISPOT assays measure the ability of activated CTLs to secrete a single cytokine, but do not provide any information on the lytic ability. Also, it has been previously demonstrated that antigen-presenting cells (APCs) displaying low density of peptide-loaded MHC (pMHC) can elicit cytotoxic function without the concurrent secretion of cytokines (Valitutti S et al. (1996) Different responses are elicited in cytotoxic T lymphocytes by different levels of T cell receptor occupancy. *J. Exp. Med.* 183, 1917). This constraint is particularly important in trying to isolate HIV-specific CTLs because viral infection down-regulates class I MHCs (Mangasarian A et al. (1999) Nef-Induced CD4 and Major Histocompatibility Complex Class I (MHC-I) Down-Regulation Are Governed by Distinct Determinants: N-Terminal Alpha Helix and Proline Repeat of Nef Selectively Regulate MHC-I Trafficking *J. Virol.* 73(3), 1964). Peptide-loaded, fluorescently-labeled HLA class I tetramer staining coupled with flow-cytometry is used to isolate antigen-specific CTLs, but again provides no information on lytic ability. Additionally, it has been shown that CTLs isolated using tetramer staining do not always recognize virus-infected cells (Appay V et al. (2000) HIV-specific CD8+ T cells produce antiviral cytokines but are impaired in cytolytic function. *J. Exp. Med.* 192(1), 63). A flow-cytometric lysis assay using caspase substrates has been reported, but is not well-suited for screening large numbers for effector cells (Liu L et al. (2002) Visualization and quantification of T cell-mediated cytotoxicity using cell-permeable fluorogenic caspase substrates *Nat. Med.* 8, 185). Thus, prior to the invention described herein, there was no single high-throughput technique that measures the ability of single CTLs to lyse single infected target primary cells and measure the cytokines and cytotoxic molecules that they secrete while still being able to retrieve the live cell to establish clonal lines for further functional characterization and genetic analysis.

The preservation of high frequencies of CD8+ T cells that are able to recognize and lyse infected CD4+ T cells correlates directly with the ability of patients to inhibit viral replication. Defining the unique phenotype, function, and gene expression profile of cytolytic versus non-cytolytic CTL on the single-cell level will allow for the definition of the correlates of antiviral CD8+ T cell immunity required for the generation of an effective HIV vaccine. The invention provides a single cell CTL killing assay combined with phenotyping and genetic analyses that will allow for the determination of immunologic and genetic correlates of effective antiviral CD8+ T cell-mediated immunity. Defining these characteristics at the single cell level will provide a prototypical response that is elicited through a vaccination designed to drive the expansion of CD8+ T cells that can control viral replication potently.

Antibody Diversity in HIV-Infected Persons

The primary receptor expressed on the surface of HIV is gp120. It is necessary for infection, and binds CD4, a receptor presented on the surface of certain T cells. Many approaches for HIV vaccines have sought to block infection by raising a NAb response against gp120, but all attempts have failed to date, due largely to the variability of the receptor among strains and its proclivity to mutate within its host. There are, however, examples of infected persons who have generated NAb naturally that broadly neutralize many variants of the virus. The diversity of these antibodies has been difficult to assess with conventional techniques because the unique antibodies in sera are limited in quantity, difficult to purify, and can not be produced recombinantly without the corresponding genes. The challenge is matching a bNAb to the clonal line of B cells from which it was produced. To date, the most successful approach to identifying genes that encode NAb has been panning antibody libraries generated recombinantly from a large number of circulating B cells from HIV+ individuals (Koefoed, K., Farnaes, L., Wang, M., Svejgaard, A., Burton, D. R. & Ditzel, H. J. Molecular characterization of the circulating anti-HIV-1 gp120-specific B cell repertoire using antibody phage display libraries generated from pre-selected HIV-1 gp120 binding PBLs. *J Immunol Methods* 297, 187-201 (2005)). These approaches obscure the natural repertoire of the individual, however, because the process scrambles the unique clonal combinations of heavy and light chains. As described in the Examples below, two issues will be addressed: (1) the clonal diversity among bNAb-producing B cells in an individual; and (2) the characteristics of bNAb that bind diverse primary isolates.

Cellular Immune Response to HIV

Hope for an HIV vaccine lies in those persons who remarkably control progression of the disease naturally—so-called 'elite controllers'—and in non-human primates protected from simian immunodeficiency virus (SIV) by vaccination, but the critical factors that correlate with protection in these cases still are not clear (Saez-Cirion, A., Pancino, G., Sinet, M., Venet, A., Lambotte, O. & Gr, A. E. H. C. S. HIV controllers: how do they tame the virus? *Trends Immunol* 28, 532-540 (2007); Decks, S. G. & Walker, B. D. Human immunodeficiency virus controllers: Mechanisms of durable virus control in the absence of antiretroviral therapy. *Immunity* 27, 406-416 (2007); Koff, W. C., Johnson, P. R., Watkins, D. I., Burton, D. R., Lifson, J. D., Hasenkrug, K. J., McDermott, A. B., Schultz, A., Zamb, T. J., Boyle, R. & Desrosiers, R. C. HIV vaccine design: insights from live attenuated SIV vaccines. *Nat Immunol* 7, 19-23 (2006)). The adaptive immune response has received much attention, but recent studies on the innate immune system have highlighted its importance for shaping the adaptive response (Pulendran, B. & Ahmed, R. Translating innate immunity into immunological memory: Implications for vaccine development. *Cell* 124, 849-863 (2006)). The existing assays for monitoring how effectively immune cells can eliminate infected cells are not sufficient to characterize the heterogeneities in their functional behaviors (Fauci, A. S., Johnston, M. I., Dieffenbach, C. W., Burton, D. R., Hammer, S. M., Hoxie, J. A., Martin, M., Overbaugh, J., Watkins, D. I., Mahmoud, A. & Greene, W. C. Perspectiv—HIV vaccine research: The way forward. *Science* 321, 530-532 (2008); Walker, B. D. & Burton, D. R. Toward an AIDS vaccine. *Science* 320, 760-764 (2008)). The invention provides methods for the characterization and correlation of multiple immune functions to individual cells of different lineages in order to analyze the subsets of effector cells from different groups of patients, e.g., acute infections, chronic progressors, highly active antiretroviral therapy (HAART) patients, and elite controllers. As described herein, quantitative cellular analyses highlight cells with specific combinations of functions necessary for controlling viral replication.

The innate immune response provides another arm of protection against viral infections. NK cells are a central component of this response (Alter, G., Teigen, N., Ahern, R., Streeck, H., Meier, A., Rosenberg, E. S. & Altfeld, M. Evolution of innate and adaptive effector cell functions during acute HIV-1 infection. *J Infect Dis* 195, 1452-1460 (2007)). These cells are cytotoxic effector cells that also induce adaptive immune responses through the release of cytokines such as IFNγ, MIP-1β, TNF-α, and GM-CSF. In the context of HIV-1 infection, strong epidemiologic data has demonstrated that individuals who possess both particular NK cell receptors (killer immunoglobulin receptor-3DS1 (KIR3DS1) and some alleles of KIR3DL1) and their putative ligand (HLA-B alleles with an isoleucine at position 80) progress more slowly towards AIDS than individuals that have only one or neither of these alleles (Martin, M. P., Qi, Y., Gao, X. J., Yamada, E., Martin, J. N., Pereyra, F., Colombo, S., Brown, E. E., Shupert, W. L., Phair, J., Goedert, J. J., Buchbinder, S., Kirk, G. D., Telenti, A., Connors, M., O'Brien, S. J., Walker, B. D., Parham, P., Deeks, S. G., McVicar, D. W. & Carrington, M. Innate partnership of HLA-B and KIR3DL1 subtypes against HIV-1. *Nat Genet.* 39, 733-740 (2007)). Similarly, elevated NK cell activity and increased expression of KIR3DS1 transcripts in bulk NK cells correlate with protection from infection despite repeated exposures (Alter, G., Martin, M. P., Teigen, N., Can, W. H., Suscovich, T. J., Schneidewind, A., Streeck, H., Waring, M., Meier, A., Brander, C., Lifson, J. D., Allen, T. M., Carrington, M. & Altfeld, M. Differential natural killer cell-mediated inhibition of HIV-1 replication based on distinct KIR/HLA subtypes. *The Journal of experimental medicine* 204, 3027-3036 (2007); Long, B. R., Ndhlovu, L. C., Oksenberg, J. R., Lanier, L. L., Hecht, F. M., Nixon, D. F. & Barbour, J. D. Conferral of enhanced natural killer cell function by KIR3DS1 in early human immunodeficiency virus type 1 infection. *J Virol* 82, 4785-4792 (2008)). These data suggest that particular NK cell populations play a protective role in both preventing and controlling infection, but the precise phenotypes of these cells remain undefined.

One mechanism used by NK cells to eliminate HIV-infected cells is direct cytolysis upon cell-to-cell contact. Some forms of the KIRs expressed on the surface of NK cells provide inhibitory signals to the cell that suppresses cytolytic function when ligated to HLA class I expressed on the surface of a target cell (Moretta, A., Bottino, C., Mingari, M. C., Biassoni, R. & Moretta, L. What is a natural killer cell? *Nat Immunol* 3, 6-8 (2002)). In the absence of these interactions, the NK cells activate and lyse the target cell. HIV-infected cells often downregulate the expression of HLA-A and -B alleles, which makes them more susceptible to cytolysis by activated NK cells (Fogli, M., Mavilio, D., Brunetta, E., Varchetta, S., Ata, K., Roby, G., Kovacs, C., Follmann, D., Pende, D., Ward, J., Barker, E., Marcenaro, E., Moretta, A. & Fauci, A. S. Lysis of endogenously infected CD4+ T cell blasts by rIL-2 activated autologous natural killer cells from HIV-infected viremic individuals. *Plos Pathogens* 4, 1-13 (2008)). A second mechanism by which a subset of NK cells that express CD16 (Fcγ receptor III) destroy HIV-infected cells is ADCC (Cooper, M. A., Fehniger, T. A. & Caligiuri, M. A. The biology of human natural killer-cell subsets. *Trends Immunol* 22, 633-640 (2001)). These receptors bind to the Fc region of antibodies bound to targets on the surfaces of infected cells, and activate lysis by the NK cell. This mechanism of protection requires cooperation between the humoral immune response mediated by B cells and the innate response of the NK cells. This response is potentially important for delayed progression of HIV infection, and in some cases, for protection from HIV-1 for intravenous drug users and from SIV in macaques (Stratov, I., Chung, A. & Kent, S. J. Robust NK cell-mediated human immunodeficiency virus (HIV)-specific antibody-dependent responses in HIV-infected subjects. *J Virol* 82, 5450-5459 (2008)). Prior to the invention described herein, investigations of this mechanism have been limited, however, by the lack of quantitative assays to measure ADCC.

The invention will be further illustrated in the following non-limiting examples.

Example 1

Development of a High-Throughput Assay for Assessing the Cytolytic Activity of Single Cells Studies have previously described a high-throughput assay to functionally characterize large numbers of primary cells by loading single cells in picoliter microwells ($\sim 2 \times 10^5$ per microarray, each well $\sim 30$ μm diameter) (Bradshaw E M et al. (2008) Concurrent detection of secreted products from human lymphocytes by microengraving: cytokines and antigen-reactive antibodies. *Clin. Immunol.* 129(1), 10; Love J C et al. (2006) A microengraving method for rapid selection of single cells producing antigen-specific antibodies. *Nat. Biotech.* 24(6), 703). The loaded microwells are held in physical contact with glass slides pre-functionalized with the appropriate reagents (for example anti-IL-2 capture antibody coated onto poly-lysine slides) and incubated for 2 h to capture the secreted cytokines. The slides are then processed and tagged with the appropriate detection antibodies to reveal fluorescent spots on the slides that can be mapped onto the cells that secreted them. The cells can subsequently be retrieved using robotic micromanipulators for clonal expansion.

The invention provides for the application of arrays of microwells to study interactions between cells. Specifically, the invention provides for the ability to monitor killing of infected target cells by single CTLs while simultaneously profiling activation markers/secreted soluble mediators. Another advantage of this assay system is the speed by which results are obtained (or the assay is completed). For example, results are obtained (or the assay is completed) in less than 24 hours, less than 12 hours, or less than 10 hours. For example, the results are obtained (or the assay is completed) in less than 4 hours.

Fabrication of Microarray Stamp

The microwell arrays are fabricated in polydimethylsiloxane (PDMS) using photolithography and replica molding. The depth and size of the well is preferably less than 100 μm, e.g., less than 50 μm. The depth and size of the well, as dictated by the master, are set to $\sim 30$ μm. $O_2$ plasma treatment is used to both sterilize the microarray and render it hydrophilic. The plasma treated array is immersed in PBS-BSA to preserve the hydrophilic character for subsequent use.

Cell Stocks

Both HIV-infected CD4 cells and autologous CD8 cells are used in the methods described below. Also utilized in the methods described below include PBMCs from progressors, LTNPs and HIV negative individuals. Additionally, isolated CTL clones that specifically recognize HLA-B27 restricted HIV gag peptide (KK10) serve as positive control to establish the validity of the assay and to refine experimental conditions.

Assay Development

In order to design a robust protocol for the isolation of target-specific CTLs, the KK10-specific clone (effector) previously mentioned are used as effectors and HLA B27-expressing, EBV-transformed B cells are used as targets. A schematic illustrating a general overview of the assay is shown in FIG. 1. The peptide loaded B cells (targets) are stained using Calcein AM (Invitrogen, Carlsabad, Calif.), a non-specific fluorescent substrate for intracellular esterases and lipases, and serve as a marker of cell integrity. Intact, non-compromised cells remain fluorescent in the absence of effector cells for the duration of the killing assay (4 h), as shown in FIG. 2A.

Since a decrease in target fluorescence is also possible due to photobleaching/fluorophore degradation upon prolonged incubation, targets are labeled using Sytox Red (Invitrogen, Carlsabad, Calif.). The Sytox family of membrane impermeable dyes show a high increase in fluorescence intensity (>500 fold) when they intercalate nucleic acids and hence can be used as specific markers for lysed cells with compromised membranes. Since the Sytox and Calcein dyes label the cells in orthogonal ways, these can be used simultaneously to monitor the kinetics of target lysis by tracking fluorescence increase/decrease in independent channels of the fluorescent microscope.

The effectors are labeled with fluorescent anti-CD8 antibodies (APC/Alexa647/Pacific Blue). The dye that shows the most reproducible signal and least photobleaching/degradation under assay conditions (4 h, 37° C.) will be used. Effectors labeled with α-CD8-APC are shown in FIG. 2B.

Figure 2:
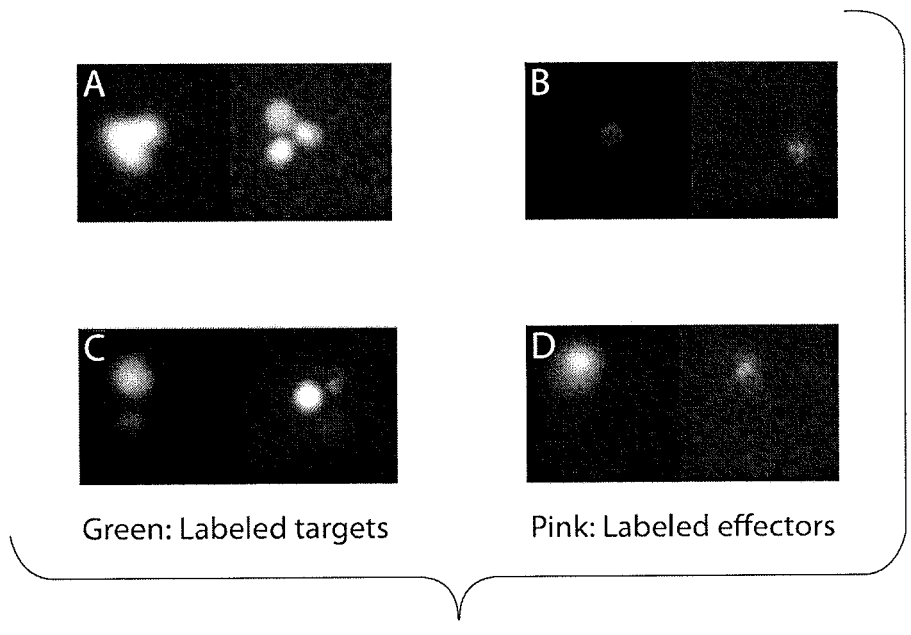
FIG. 2 is series of representative fluorescent images of labeled targets and effectors pre and post-incubation (0 and 4 h). (A) Calcein stained (green), peptide loaded (KK10) targets (3 individual cells can be seen); (B) effectors labeled (pink) with α-CD8-APC; (C) co-incubation of effectors (pink) and unloaded (no KK10 peptide added) targets (green); (D) co-incubation of effectors (pink) and targets (green) loaded with KK10 peptide. Target-lysis occurs only when effectors recognize peptide loaded targets (shown in D).

Both previous reports (Bradshaw E M et al. (2008) Concurrent detection of secreted products from human lymphocytes by microengraving: cytokines and antigen-reactive antibodies. *Clin. Immunol.* 129(1), 10; Love J C et al. (2006) A microengraving method for rapid selection of single cells producing antigen-specific antibodies. *Nat. Biotech.* 24(6), 703) and preliminary experiments (FIGS. 2A & 2B) confirmed that the cells do not undergo apoptosis when encapsulated in the microwells. The optimal ways to load the microwell arrays with defined ratios of targets and effectors was next determined. Two different approaches, pre-mixing the targets and effectors in media prior to loading or sequential loading of effectors and targets, were evaluated. Since the sequential loading of effectors first, followed by targets, afforded better control over effector:target ratio manipulation in microwells, this was adopted as the standard approach. To explore the feasibility of the assay, unloaded targets (targets with no peptide bound, negative control) and KK10 loaded targets (positive control) were incubated with effectors. Since the T cell receptor (TCR) on the effector can recognize only the pMHC on the target, no lysis was observed in the absence of the peptide (FIG. 2C). When the targets were pre-loaded with KK10 peptide and incubated with effectors, lysis of the targets, as demonstrated by the loss of green fluorescence, was observed (FIG. 2D). The data shown in FIG. 2 is representative data from one single microwell. In order to estimate the frequency of microwells that had a single target incubated with a single effector and to determine the frequency of the subset of effectors that did specifically lyse the targets, automated analysis of the fluorescent images (two different channels) and the phase contrast image (transmitted light, third channel) generated is essential. For experiments involving controls using targets and effector clones as described above manual inspection of small numbers of cells ($\sim 10^2$) was sufficient to ascertain the validity of the assay, but for routine screening, algorithms for extracting and analyzing the resulting data stack will be necessary.

Identification of Low-Frequency Cells

An important requirement for the successful implementation of the assay for routine screening of CTLs is the ability to detect and isolate low frequency positives. Towards this goal, effectors are premixed towards HLA-B27 KK10 (labeled with Calcein Blue) with effectors towards an irrelevant eptiope (unlabeled) at different ratios (1/5,000-1/25,000), label the mixture of cells with α-CD8-APC and incubate them with KK10 loaded targets (labeled with Calcein green) in microwell arrays. Low-frequency effector positives are identified in microwells by the loss of green fluorescence of targets by KK10-specific effectors and the ability to map these can be independently verified by identifying the location of KK10-specific effectors via fluorescence images obtained in the blue channel of the microscope.

Defining the Phenotype of Antiviral CTL Activity

The microwell-array platform is adopted to dissect the biology of effective CTL-mediated killing. HIV-infected target cells (T) as well as effector cells (E) are labeled with two different fluorescent reporter dyes and mixed at various E:T ratios, and then loaded onto an array of microwells in such a way that a single effector is deposited on average into each well. The cells are cocultured for 4 h, and then cytolysis is measured by detecting the loss of target cell fluorescence over time. Ultimately, cells that mediated killing are identified, and these cells are retrieved using an automated micromanipulator and transferred directly into RNA extraction buffer. In parallel, intermediate killers and non-killers also are retrieved, for comparison. In a subset of experiments, killers and non-killers are picked and used for single cell cloning to gain in-depth knowledge about these cells at the clonal level. This assay allows for the characterization of CTLs in a more detailed manner, but also allows for the performance of these assays on non-manipulated T cells to gain a clear idea of the ex vivo correlates for protective CD8+ T cell responses. These assays are amenable to various experimental modifications allowing for the definition of the differences between the phenotypes of effector CTLs from controllers versus progressors or patients with 'protective' versus 'nonprotective' HLA alleles.

Figure 4:
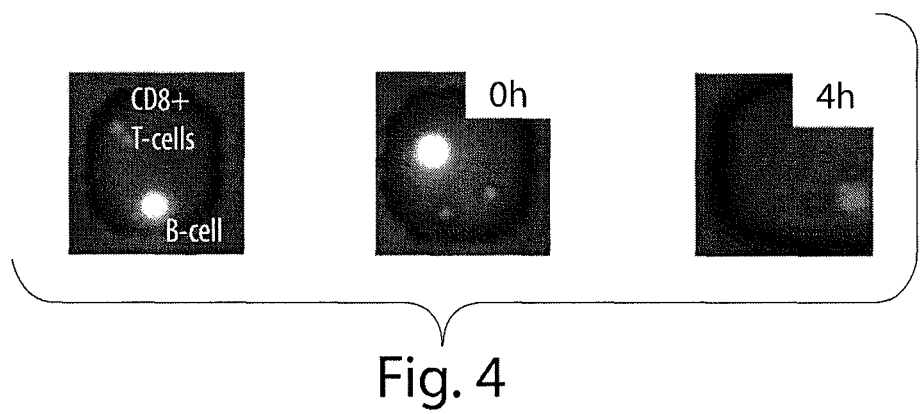
FIG. 4 is a series of fluorescent images showing co-culture of HIV-specific CD8+ T-cell clones with Calcein AM-labeled HIV peptide loaded B-cells. CTL mediated lysis is marked by a loss of fluorescence signal.
Figure 5:
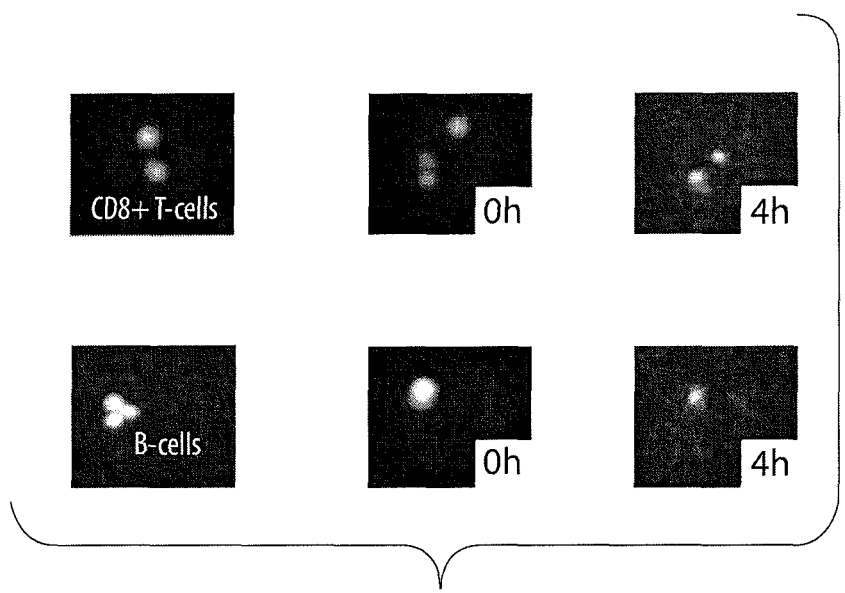
FIG. 5 is a panel of fluorescent images showing co-culture of APC-labeled CTLs (red) and Calcein AM labeled B-cells (green). Calcein AM fluorescence quenching represents CTL mediated killing.

Establish a Microwell-Based Assay for Assessing the Cytolytic Capability of Single Cells The invention also provides for the identification of cell-mediated killing in different settings with high reproducibility. Numerous details associated with the above-mentioned micro-well plates remain to be defined, including the biological design, reagents, kinetics, cell preparation, choice of target cell, and data analysis. The assay is defined using cytolytic T cell clones as effectors and peptide-pulsed B cells as targets. In a preliminary experiment, HLA B27-expressing B cells were pulsed with a HIV gag peptide (KK10) and then labeled with Calcein AM. Target cells were co-cultured with a CTL clone recognizing the B27-KK10 epitope (E:T=1:1) and after incubation for 4 h, lysis was detected by loss of fluorescence from the target cell (FIG. 4). Different labeling approaches are evaluated using a range of dyes to highlight both effector and target cells, and adjust ratios of E:T per well to improve visualization of cytolytic activity. In another preliminary experiment, effector cells were labeled with anti-CD8-APC and B cells with Calcein AM. FIG. 5 illustrates the progressive loss of target cells over 4 hours of co-culture. Effector cells (red) are clearly differentiated from target cells (green).
Develop Software Algorithms to Identify Cells of Interest.

The refinement of the protocol developed allows routine screening of $10^5$-$10^6$ cells per experiment. The data generated from one array will comprise 24*72*3 images (~5 Gb of data). The optimization of the assay is be accomplished by manual inspection of small numbers of cells ($10^2$-$10^3$), but for routine screening by this method, algorithms for extracting and analyzing the resulting data stack is preferable. A software approach is developed to address the bioinformatics. A custom package is developed for image analysis to process and store the large amounts of data that will accumulate with each array. The software recognizes wells where killing took place and locate those wells for the micromanipulator.

Example 2

Figure 3:
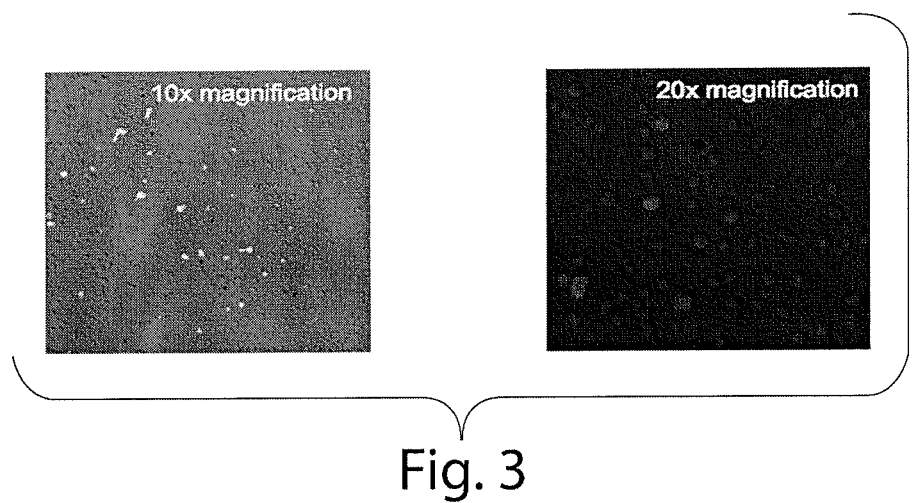
FIG. 3 is a panel of fluorescent images of CD4 T-cells infected with a GFP-expressing NL4-3 virus. The green cells mark infection.

Identification and Isolation of CTLs Specific for HIV-Infected CD4+ T Cells Via their Ability to Lyse the Target Cells and Detect Secreted Mediators of these CTLs Once the optimal conditions for the identification of low-frequency cells has been established, microwell assay is used to identify CTLs that are able to lyse HIV-infected autologous CD4+ T cells. The initial strategy uses CD4+ T cells infected with GFP-expressing recombinant viruses to specifically visualize the preferential killing. Flow-cytometric sorting on GFP fluorescence would also ensure a homogeneous viral infected CD4+ target population. Recent studies have evaluated GFP+NL4-3-derived HIV variants for infectivity, replicative capacity, and GFP signal intensity with promising results. CD4 T-cells show a distinct green fluorescence signal when infected with these GFP-expressing strains (FIG. 3). Purifying infected CD4 cells by cell sorting guarantees a homogeneous target population.
Detect Secreted Mediators of Target-Specific Lytic CTLs Microengraving technology has been developed for the multiplexed detection of secreted cytokines (Bradshaw E M et al. (2008) Concurrent detection of secreted products from human lymphocytes by microengraving: cytokines and antigen-reactive antibodies. *Clin. Immunol.* 129(1), 10). As illustrated in FIG. 1, glass slides pre-functionalized with capture antibodies against cytokines are placed in contact with the microwell array. After incubation, the slides are washed and detected with fluorophore conjugated detection antibodies. The spots are mapped to individual wells in the microwell array to enable identification and picking of the cells contained within the microwell. In the context of CTL mediated killing, secretion of TNF-α, IFN-γ and the soluble mediators of lysis, granzyme B (GzB) and perforin will be detected. The detection of GzB and perform may be challenging since their secretion is polarized towards the immunological synapse (IS) (Faroudi et al. (2003) Lytic versus stimulatory synapse in cytotoxic T lymphocyte/target cell interaction: manifestation of a dual activation threshold. *Proc. Natl. Acad. Sci. USA* 100, 14145) and because the amount secreted is typically small. In the event that the amount of secreted factors is too low for detection using the assay, CTL activation is monitored by tracking intracellular calcium levels. TCR triggering by pMHC complexes leads to a dose-dependent increase in cytosolic calcium ion concentration in T cells (Kim H et al. (2006) Live lymphocyte arrays for biosensing *Adv. Funct. Mater.* 16, 1313). Membrane-permeable calcium-sensitive fluorescent dyes like Fura 2AM (Invitrogen) can function as convenient reporters of intracellular calcium levels and thus T cell activation. Should both of these options seem non-viable, the effector cells are labeled for the activation marker, CD69.

After the characterization of the CTLs via lytic ability, secreted factors and activation state, the cells are then retrieved using a micromanipulator for establishing clonal lines and to provide genetic information. If cell loss during cytokine printing is a problem, alternate ways to capture and retain cells in microwell arrays using fibronectin/anti-CD44 (B/T cell surface marker), as opposed to just gravity will be explored.

Example 3

Differences in CTLs Between Disease Progressors and Long-Term Non-Progressors (LTNPS) Measured by their Ability to Secrete Soluble Mediators and the Ability to Effect Lysis This research aims to quantify and compare the Cytotoxic T Lymphocyte (CTL) responses to HIV-infected CD4+ T cells, both, by their ability to lyse their targets and by their ability to secrete cytokines. The approach is based on the recently developed high-throughput screening methodology to profile large numbers of single cells in microarrays and is applied to analyze interactions between pairs of target and effector cells.
Compare and Quantify the Differences in CTLs The invention provides for the ability to quantify differences between individual target specific CTLs in large populations of progressors, LTNPs, infected individuals on HAART, and chronically infected individuals. For example, although a significant difference in perforin expression and proliferation of HIV-specific CTLs in LTNPs and progressors has been shown, the analysis was done on populations of CTLs and no direct information was available on the lytic properties of these cells (Migueles S A et al. (2002) HIV-specific CD8+ T cell proliferation is coupled to perforin expression and is maintained in non-progressors *Nat. Immun.* 3(11), 1061). An important question that arises is whether there are subsets of CTLs which undergo activation by TCR ligation, but are impaired in their secretory response, either cytokines or cytotoxic agents. High-throughput assay is able to identify these and other subsets of CTLs and help retrieve the cells for subsequent establishment of clonal lines and genetic manipulation.

This results in a robust, quantitative assay to identify and retrieve CTLs able to lyse HIV-infected cells on a single cell level. This approach would not only quantify killing, but would also allow for detailed insights into the immunologic and genetic correlates of effective antiviral CTL function upon subsequent retrieval by micromanipulation. This technology comprehensively defines many of the characteristics of CTL biology and allows for the rapid evaluation of large patient populations of acutely-infected patients, HAART-treated patients, elite controllers, and chronically infected patients to assess the differences in CTLs in these groups. Furthermore this assay is easily extended to study killing by various cell subsets including cytolytic cells (ie. natural killer cells. macrophages, etc.).

Example 4

Evaluation of Antibody Diversity in HIV-Infected Persons

Figure 6:
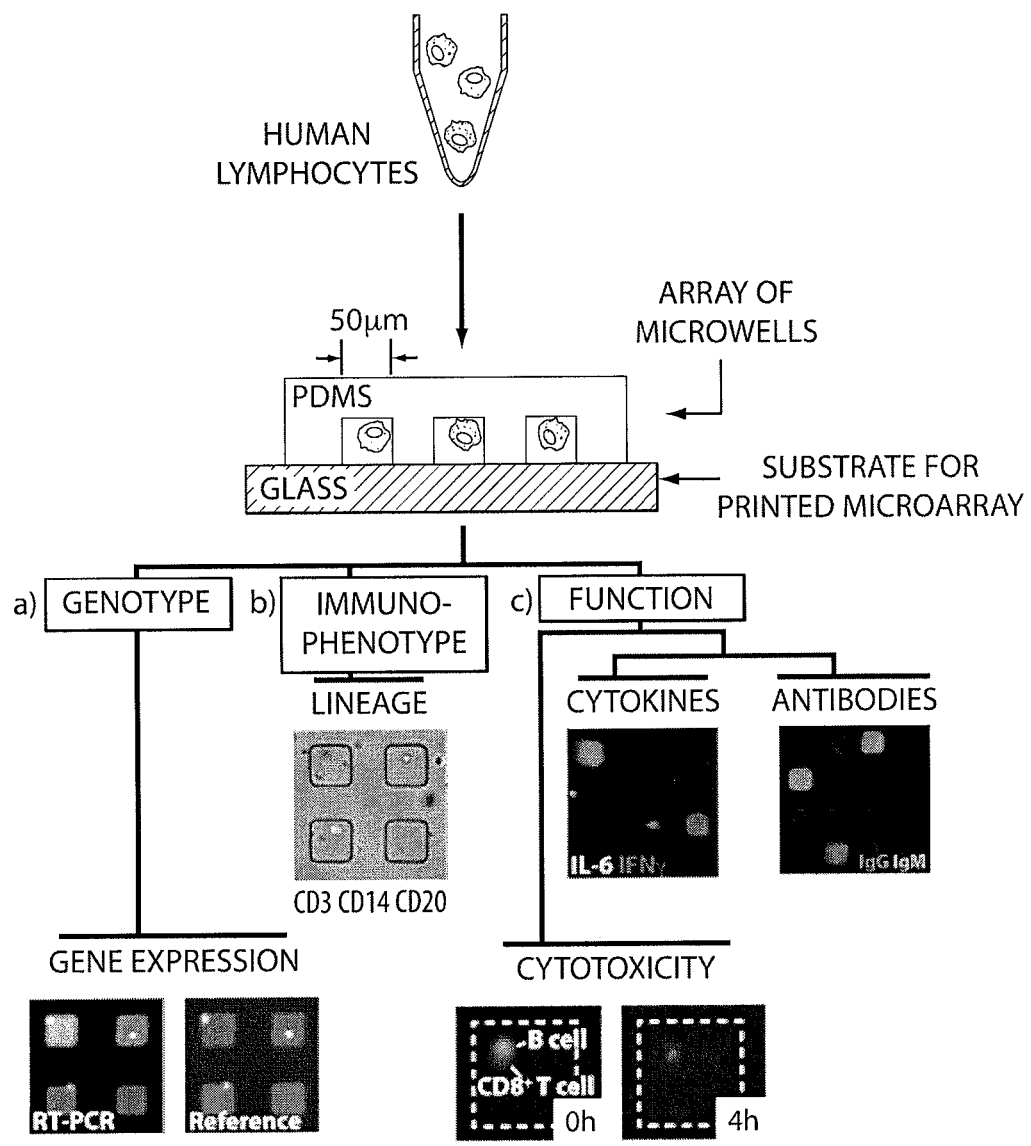
FIG. 6 is a schematic depicting the suit of single-cell measurements that has been developed using an array of microwells. Measurements are coupled in series or in parallel. The squares shown in each image are 50 μm.

Presented herein is a suite of new methods using microfabricated systems to assess multiple characteristics of many primary individual lymphocytes in parallel. These techniques enable identifying antigen-reactive antibody-secreting cells, (Love, J. C., Ronan, J. L., Grotenbreg, G. M., van der Veen, A. G. & Ploegh, H. L. A microengraving method for rapid selection of single cells producing antigen-specific antibodies. *Nat Biotechnol* 24, 703-707 (2006); Ronan, J. L., Story, C. M., Papa, E. & Love, J. C. Optimization of the surfaces used to capture antibodies from single hybridomas reduces the time required for microengraving. *J. Immunol. Methods* (in press); Story, C. M., Papa, E., Hu, C.-C. A., Ronan, J. L., Herlihy, K., Ploegh, H. L. & Love, J. C. Profiling antibody responses by multiparametric analysis of single B cells. *Proc. Natl. Acad. Sci,* 105, 17902-17907 (2008)) profiling secreted cytokines, (Bradshaw, E. M., Kent, S. C., Tripuraneni, V., Orban, T., Ploegh, H. L., Hafler, D. A. & Love, J. C. Concurrent detection of secreted products from human lymphocytes by microengraving: antigen-reactive antibodies and cytokines. *Clin Immunol* 129, 10-18 (2008).) amplifying mRNA transcripts, and assessing cytotoxic function—with single-cell resolution (FIG. 6). The common element used for these techniques is a dense array of sub-nanoliter microwells molded into the surface of a polymeric chip ($\sim 10^5$-$10^6$ wells per chip). Cells are deposited from a suspension at a density of $\sim 1$ cell per well (e.g., 1, 2, 3, 4, or 5 cells/well, preferably 1 cell per well). The array of cells can act both as a stamp to print protein microarrays of secreted molecules (antibodies or cytokines) and as a set of containers for defined single-cell assays (gene expression, cytotoxicity, or proliferation). Except for assessing gene expression, the cells remain viable after the assays: surface-expressed markers can be imaged to determine immunophenotypes, and cells of interest are retrieved by micromanipulation for clonal expansion or genetic analysis. Sequential application of these assays correlate the function, immunophenotype, and genotype to the same set of single cells. Together, these measurements yield data similar to that obtained by population-based assays for function (ELISA, ELISpot, proliferation), phenotype (FACS, immunofluorescence), and genotype (RT-PCR), but with single-cell resolution.

The Clonal Diversity Among bNAb-Producing B Cells in an Individual

Figure 7:
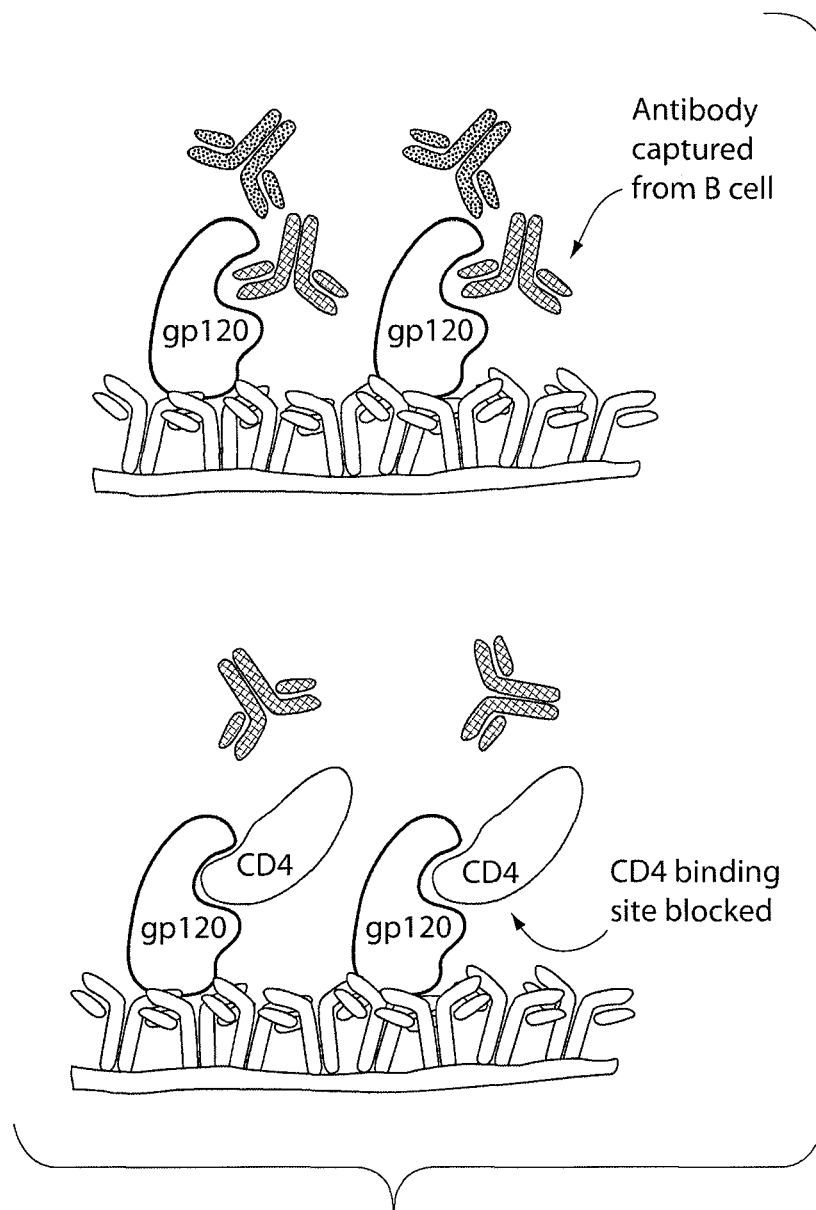
FIG. 7 is a schematic illustration of the capture assay for identifying cells that recognize the CD4 binding region of gp120. One array of B cells will be used to print (a) on a surface of immobilized gp120, and then (b) on a second surface of immobilized gp120, after blocking with soluble CD4.

Microengraving is a technique that has been developed for printing microarrays of antibodies from single cells to quantify the frequency of gp120-reactive circulating B cells, the distribution of the isotypes of their antibodies, and their neutralizing abilities. The screening assay is configured to highlight gp120-reactive antibodies by first immobilizing an antibody specific for the c-terminus of gp120 (D73-324) on the surface of a glass slide, and then depositing recombinant gp120 (Progenies). B cells from HIV+ individuals, who have high titers of bNAbs in their sera, are simulated with CD40L/anti-BCR to induce antibody production. The cells are deposited into an array of microwells and used to print two replicate microarrays of antibodies on the gp120-coated slides. Prior to printing the second array, either soluble CD4 or b12 (a monoclonal antibody with known neutralizing abilities) is added to the substrate used to capture antibodies from the cells. Antibodies that bind gp120 on the first microarray, but that fail to bind to the CD4-blocked gp120 on the second array, will likely neutralize HIV (FIG. 7). To score the diversity of isotypes present, the microarrays are labeled with a mixture of fluorescent, isotype-specific secondary antibodies (IgG1, IgG3, IgG4, IgA, IgM). Antibodies of interest on the microarrays are mapped to the corresponding microwell, and the cell retrieved by automated micromanipulation (Aviso CellCelector). The variable regions of the genes encoding the heavy and light chains are amplified and sequenced by single-cell RT-PCR (Wang, X. W. & Stollar, B. D. Human immunoglobulin variable region gene analysis by single cell RT-PCR. *J Immunol Methods* 244, 217-225 (2000)). Comparison of the sequences links closely related clones through the dominant germline genes and somatic mutations. The antibodies are recombinantly expressed and their neutralizing abilities are verified with standard assays (Monogram Biosciences).

Characteristics of bNAb that Bind Diverse Primary Isolates

Figure 8:
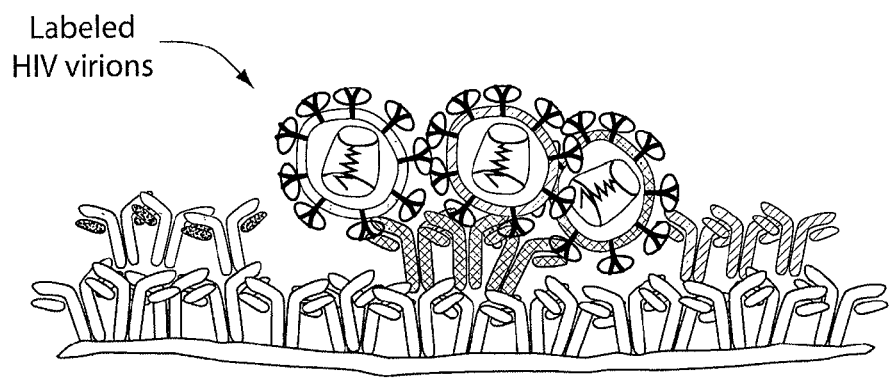
FIG. 8 is a schematic illustration of experimental design for identifying human antibodies from B cells that bind multiple HIV strains. Each cluster of captured antibodies (colored) represents one element of the microarray that matches to a cell held in a corresponding array of microwells.
Figure 9:
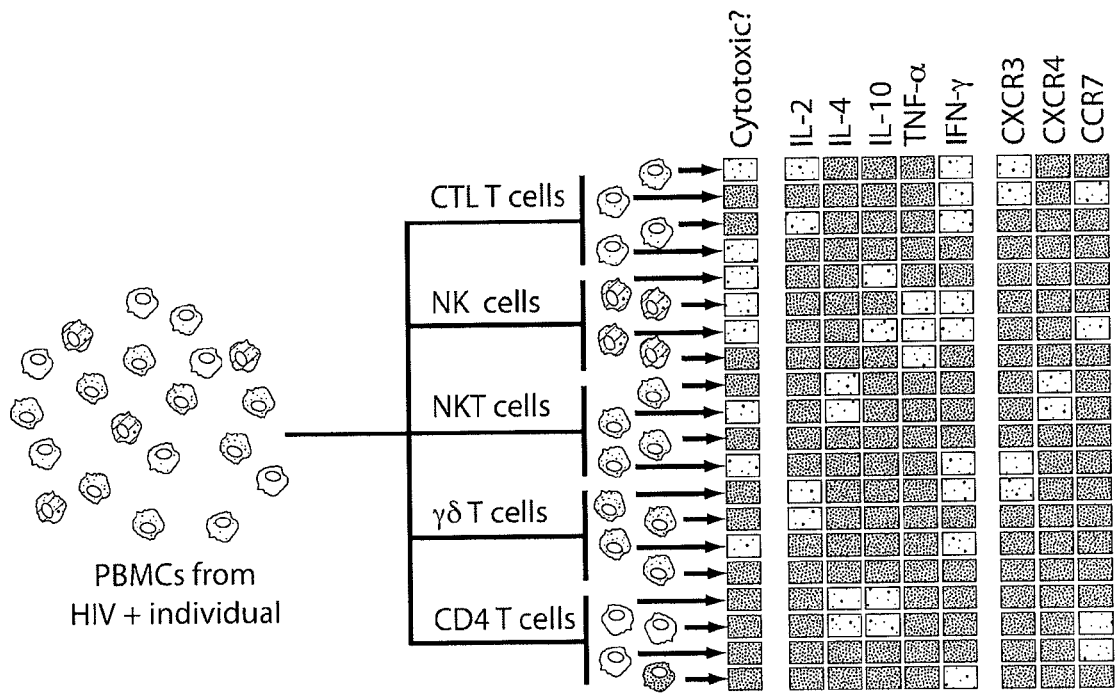
FIG. 9 depicts the construction of a functional profile from single-cell data. Populations of cells are sorted and their cytotoxic abilities, their cytokine profiles, and surface markers are measured. Such maps indicate how the frequencies of subsets change through the course of infection. Similar profiles for CD4+ T cells provide point of reference for the state of the system.
Figure 10:
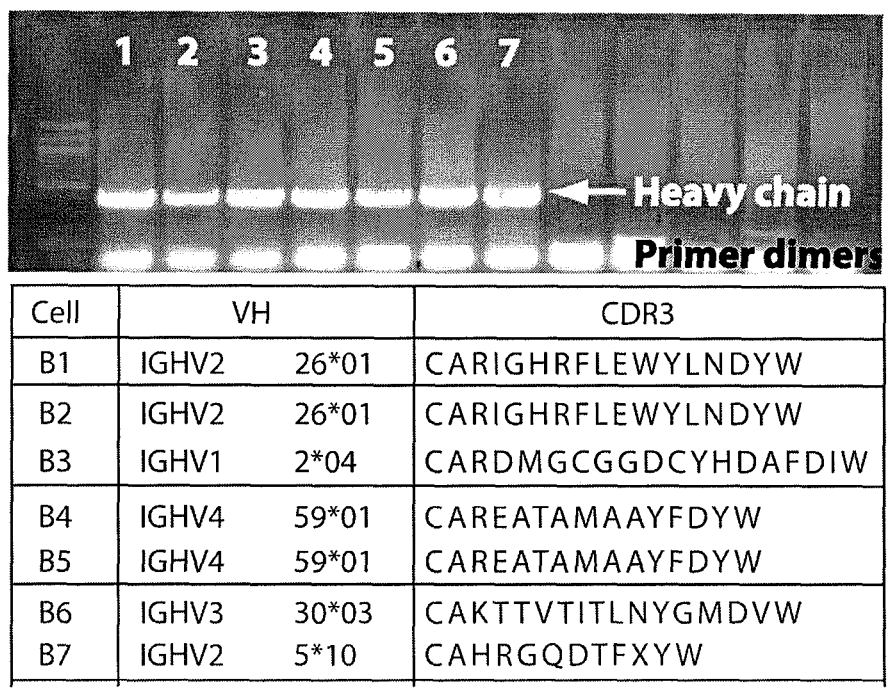
FIG. 10 shows a gel illustrating the results of degenerate RT-PCR of individual B lymphocytes selected from microwells. B cells were purified from a blood sample (negative selection of PBMCs by magnetic sorting) and loaded into microwells. Cells from twelve microwells were selected at random, deposited into lysis buffer, and amplified by RT-PCR using a degenerate set of primers for the heavy and light chains. Seven protein sequences (SEQ ID NOS 1, 1-3 and 3-5, respectively, in order of appearance) were retrieved and are shown below the gel.

One challenge for vaccines designed to raise NAbs is that the immunogens must elicit antibodies that broadly cross-react with other variants of the virus. Understanding the specificities of antibodies that neutralize diverse primary isolates would guide the design of new immunogens, and is one of the current priorities for research in HIV (Fauci, A. S., Johnston, M. I., Dieffenbach, C. W., Burton, D. R., Hammer, S. M., Hoxie, J. A., Martin, M., Overbaugh, J., Watkins, D. I., Mahmoud, A. & Greene, W. C. Perspective—HIV vaccine research: The way forward. *Science* 321, 530-532 (2008)). Screening assay are reconfigured to capture secreted antibodies from individual B cells by microengraving, and then pan the array with different isolates of HIV—each one stained with a distinct lipophilic fluorescent dye (FIG. 8). Cells of interest are retrieved and their antibodies are expressed recombinantly and characterized for epitope specificity and neutralization abilities.

The frequency of the desired B cells may be low in circulation. Although the current limit of detection (0.01 to 0.001%) exceeds that typical for FACS (0.1%), (Bradshaw, E. M., Kent, S. C., Tripuraneni, V., Orban, T., Ploegh, H. L., Hafler, D. A. & Love, J. C. Concurrent detection of secreted products from human lymphocytes by microengraving: antigen-reactive antibodies and cytokines. *Clin Immunol* 129, 10-18 (2008)), it may be necessary to enrich gp120-reactive B cells using gp120-coated magnetic beads. Two alternative approaches to the screening assays include i) the use of cell lines or virus-like particles expressing trimeric gp120 to identify trimer-specific antibodies, and ii) competition assays with other bNAbs such as 2G12. The approaches proposed here enable a set of simple assays to monitor the ability of designed immunogens to raise antibodies that bind diverse primary isolates directly from circulating B cells.

The most common assay for assessing the response of effector cells is detection of interferon-γ (IFN-γ) by ELISpot, but this single-parameter measure does not correlate with control of viremia (Walker, B. D. & Burton, D. R. Toward an AIDS vaccine. *Science* 320, 760-764 (2008)). Measures of other functional responses, e.g., proliferation, broad cytokine profiles, markers for recruitment to mucosa, and cytolytic activity, are also needed (Fauci, A. S., Johnston, M. I., Dieffenbach, C. W., Burton, D. R., Hammer, S. M., Hoxie, J. A., Martin, M., Overbaugh, J., Watkins, D. I., Mahmoud, A. & Greene, W. C. Perspective—HIV vaccine research: The way forward. *Science* 321, 530-532 (2008)). A multiparametric functional profile is defined for different subsets of effector cells ($CD8^+$ cytotoxic T cells (CTL), natural killer (NK) cells, NK T cells, γδ T cells) that respond to HIV-infected cells using the microtools. PBMCs are sorted by FACS into CTLs ($CD8^+$), NK cells ($CD16^+$), NK T cells ($CD1d^+, V\alpha 24^+$), and γδ T cells ($V\gamma 9^+, V\delta 2^+$). Each effector subset will be co-loaded into microwells with target cells—HLA-matched, EBV-transformed B cells loaded with overlapping pools of HIV-derived peptides and stained with Calcein AM. The co-loaded arrays are imaged on a live-cell microscope to determine dual-loaded wells. After incubation, the arrays are re-imaged to assess cytotoxicity (marked by release of Calcein AM) (FIG. 6*c*, bottom right). The cytokines released by the cells that remain in the wells are profiled using microengraving (IL-2, IL-4, IL-10, TNF-α, and IFN-γ). This initial panel measures Th1 and Th2 cytokines as well as regulatory cytokines at approximately 10-15 cytokines per assay. The cells are also labeled for up to 3 specific surface markers indicating their homing patterns (e.g., CD62L, CXCR3, CCR4, CCR7) and image by micro-scopy. Cells of interest from the experiment are extracted by micromanipulation for clonal expansion or gene expression profiling. The experiments are repeated at 3-5 time points during the acute stage of infection for 5 individuals. The measurements are expanded to HAART patients and elite controllers for comparison. These data show variations in the polyfunctional responses of these populations of cells during the course of infection, and establish phenotypic traits that correlate with effective cytotoxicity. The Systems-Level Profile of the Immune Response to HIV in Elite Controllers Compared to that of Patients with Acute Infections and Those on HAART The complexity of the immune system combined with the lack of tools to monitor small functional and phenotypic differences among subsets of cells within broad classes (e.g., $CD4^+$ T cells) has restricted the majority of studies in human disease to characterizations of one population of cells isolated from the rest of the network. Systems-level quantitative analyses and predictive modeling of complex biological networks are possible, but require sufficient multivariate data to resolve the fine details of the system. State-based maps are constructed from single-cell data that describe the functional profiles for the effector subsets of cells from elite controllers, acutely-infected patients, and those on HAART (FIG. 4). Statistical analyses such as hierarchical clustering and principal-components analysis are employed to examine variations among the populations from each class. The data collected is used in the first part of this project to construct these profiles. The approach is similar to that used in integrative genomic analysis, but uses detailed single-cell data to define the resulting profiles instead (Bradshaw, E. M., Kent, S. C., Tripuraneni, V., Orban, T., Ploegh, H. L., Hafler, D. A. & Love, J. C. Concurrent detection of secreted products from human lymphocytes by microengraving: antigen-reactive antibodies and cytokines. *Clin Immunol* 129, 10-18 (2008)).

One advantage of the methods described herein is that small numbers of cells can be employed for the assays ($10^3$-$10^5$). The use of pooled peptides to load the target cells could bias the functional profiles measured. As an alternative approach, the use of autologous HIV-infected $CD4^+$ T cells is explored in these assays; it will be necessary to assess the cytokine profiles of these cells first to avoid convoluting their profiles with the cytolytic cells. The current efficiency for cloning non-cytolytic human T cells is ~75-90%. The efficiency may diminish as some cytolytic cells may undergo programmed cell death, but the cells are expanded so further analyses may be performed on each clone. Defining the fine functional differences correlated to effective antiviral responses for cells of the innate system and effector memory cells would establish benchmark criteria for evaluating vaccines or other interventions.

Example 5

The Correlation Between Phenotypic Markers and the Functional Behaviors of NK Cells During the Acute Stages of HIV Infection The assays described above are applied for multiplexed detection of cytokines secreted by single cells to generate detailed phenotypic, functional, and genotypic profiles for NK cells from both patients with acute HIV infections and long-term, non-progressors. As outlined above, the approaches are unconventional in resolving cellular contributions to a host's immune response, but one that identifies the characteristics of rare cells that can be difficult to assess by existing tools such as flow cytometry and ELISpot. Distinct subsets of NK cells are present at different stages of infection, and their functional behaviors (or loss of function) provide insight into the diminished effect of these cells after the acute stage of infection.

The cells required for this research are circulating NK cells from $HIV^+$ patients. Longitudinal samples from both acutely infected patients and long-term non-progressors/elite controllers are utilized.

There are two important subsets of NK cells reported in humans (Cooper, M. A., Fehniger, T. A. & Caligiuri, M. A. The biology of human natural killer-cell subsets. *Trends Immunol* 22, 633-640 (2001)). Cytolytic NK cells ($NKp46^{pos}CD3^{neg}CD56^{pos}CD16^{pos/neg}$) secrete large amounts of IFN-γ, TNF-α, MIP-1β, GM-CSF. By contrast, immunoregulatory NK cells ($NKp46^{pos}CD3^{neg}CD56^{pos/neg}CD16^{pos}$) produce large quantities of IL-10 and IL-17. Healthy individuals usually possess large numbers of cytolytic NK cells and low levels of immunoregulatory NK cells. However, during both pregnancy and the containment of mucosal infections, the populations of immunoregulatory NK cells expand. It is uncertain whether the balance between these two populations of NK cells changes during HIV-1 infection, and whether particular clones of NK cells are able to produce patterns of cytokines associated with multiple T-helper responses.

The microengraving method described above is utilized to detect five cytokines in a single assay (IFN-γ, TNF-α, MIP-1β, IL-10 and IL-17). To optimize the assay, NK cells are extracted from the peripheral blood of healthy controls by negative selection (Stem Cell Technologies). These NK cells are separated into two fractions, and either co-cultured with IL-12 and IL-18 (potent stimuli for all NK cell functions) or remain unstimulated. After stimulation for 4 h, NK cells are deposited onto an array of microwells (~$10^5$ 30 μm diameter wells). Kinetic studies are performed to assess the optimal incubation time to measure peak NK cell function. After capturing the cytokines on the glass, the cells in the wells are stained for prototypical markers of NK cell activation (Hoescht 33324 (nuclear), NKp46-Cy3, CD107a-Alexa647, and CD69-Alexa488), and imaged on a custom-built, high-speed imaging station. The detected cytokine profiles from each cell is correlated with these data, and clustered by principal-components analysis to identify common subsets of cells (8 parameters per cell). NK cells are isolated from 10 acutely-infected HIV patients as well as 10 long-term, non-progressors. The assays are repeated to evaluate how the subsets of cells vary in these groups compared to each other and the control set. Finally, the differences are examined in the subsets of cells present from acutely infected patients longitudinally to assess how the subsets change with progression of the disease.

Example 6

Assessing Clonal Diversity Among Cytolytic NK Cells

Unlike T and B cells that express a single antigen specific receptor, NK cells express many different receptors, in random combinations. The combination of receptors on individual NK cell clones allows them to recognize virally infected or malignant cells differentially. Both the expression of NK cell receptors and the distribution of subsets of NK cells change dramatically with HIV infection. Individuals with acute HIV-1 infection exhibit a significant expansion of NK cells: up to 50% of the circulating peripheral blood mononuclear cells (PBMC) are NK cells during the first few weeks of infection. By comparison, progressive infection is marked by the accumulation of anergic $CD56^{neg}$ NK cells. How the variety of receptors varies clonally, and how it correlates with NK cell function to enable antiviral control, are poorly understood, especially on those clones that exhibit pronounced cytolytic capabilities.

Profiles of killer cell immunoglobulin-like receptors (KIR) expressed by individual cytolytic NK cells at different stages of HIV-1 infection are determined, starting with acute infection. An assay using arrays of microwells is used to measure cytolytic function. Individual cytotoxic NK cells are retrieved by micromanipulation for subsequent quantification of their repertoire of receptors by RT-qPCR. For the single-cell cytolytic assay, NK cells labeled with CD56-Alexa 647 or a cytosolic stain (CellTracker red) are co-loaded with MHC-devoid target cells (K562 or 221) labeled with Calcein AM. These arrays are incubated for 5-6 h while imaging periodically to assess for lysis (marked by loss of Calcein from target cells). To ensure activation CD107a on the surface of the NK cells is also attained.

Preliminary results for this type of assay using CTLs and a target B cell line are shown in FIG. 5. Autologous, HIV-infected $CD4^+$ T cells as targets in this assay are alternatively used. After scoring the location of the wells containing individual lytic cells within the array, cells are retrieved by automate micromanipulation (Aviso CellCelector), and expanded clonally in 96-well plates using recombinant IL-2. Following expansion a panel of specific primers for 12 KIR are used to quantify the NK cell receptor repertoire on each clone by RT-qPCR.

Direct single-cell analysis of cells without expansion is performed by placing the cells in SuperScript-3 RT-PCR mastermix (Invitrogen) containing a set of oligo-dt primers with embedded amplification binding sequences for nested-primers, followed by thermocycling. qPCR is performed on cDNAs using the set of 12 KIR primers. The diversity in the repertoires of KIRs from isolated NK cells will be defined in 10 healthy controls, 10 acutely HIV+ infected individuals, 10 HIV+ spontaneous non-progressors (viral loads below 2000 copies/ml), and 10 HIV+ chronic untreated progressors (viral loads >10,000 copies/ml).

Example 7

Determining the Capacity of NK Cells to Effect Antibody-Dependent Cellular Cytotoxicity (ADCC) Change with Progression of Infection Most of the candidate vaccines for HIV to date have attempted to elicit broadly neutralizing antibodies to the virus (Barouch, D. H. Challenges in the development of an HIV-1 vaccine. Nature 455, 613-619 (2008)). An alternative strategy for employing an antibody response to mediate protection is ADCC. Serum-transfer studies from acutely infected patients suggest that activation of NK cells can occur, but there are heretofore no assays available for identifying B cell clones that make antibodies that effectively induce ADCC mediated by NK cells. Generating recombinant antibodies from such clones as described belos facilitates new studies on the rationale design of immunogens for vaccination (Walker, B. D. & Burton, D. R. Toward an AIDS vaccine. Science 320, 760-764 (2008)).

Three populations of cells are isolated from acutely infected patients and from long-term, non-progressors— $CD56^{low}CD16^+$ NK cells, $CD4^+$ T cells, and $CD20^+$ B cells. The $CD4^+$ T cells are expanded by culture with phytohemoagglutinin (PHA) and IL-2, and exogenously infect with HIV. The NK cells are activated with IL-2, and the B cells by CD40L and anti-BCR. B cells (labeled with CellTracker red) are co-loaded with HIV-infected T cells (labeled with Calcein AM) into an array of microwells. The array is sealed against a glass slide for one hour. During this time in the isolated reactors, the B cells produce antibodies that may bind to the surface of the infected T cells. The array is then be removed from the glass and washed.

The activated NK cells (labeled with Celltracker blue) are added to the wells and incubated for 4-6 h. The array is imaged before and after incubation to score wells that contain 1) a B cell, 2) a NK cell, and 3) a lysed T cell after incubation. Cells are retrieved from these wells and RT-PCR is performed using a degenerate set of primers for the VDJ regions of the genes encoding the antibody. Internal controls on the array are wells that randomly contain no B cell or no NK cell. Arrays with NK cells and T cells only also scored. Recombinant expression of the antibodies retrieved enable mapping of the epitopes bound on infected cells, and assessment of clonal diversity raised in the B cells that correlate to productive ADCC.

An alternative approach is to split the assay into two parts. First, enriched population of B cells to are produced using the microengraving technique and used generate microarrays of antibodies. These arrays are stained with lysates from HIV-infected cells and anti-IgG3. B cells that map to double positive wells are retrieved for genetic analysis. Recombinant antibodies from these cells are applied to infected cells and mixed with NK cells in a cytolytic assay like that described above.

The approaches described herein allow for characterizations of host-pathogen interactions directly in cells taken directly from clinical human samples, and improve the development of vaccines and immunotherapies for infectious diseases using quantitative immunological profiling for discovery, assessment, and monitoring. In addition to HIV, the approach can be extended to other infectious diseases, including pathogens that are leading causes of infection in immunocompromised persons, whether as a result of HIV or deliberate suppressive interventions. These include, e.g., *Cryptococcus neoformans, Clostridium difficile, Streptococcus pneumoniae*, and *Mycobacterium tuberculosis*.

Additional embodiments are within the claims.

What is claimed is:

1. A method of assessing cytotoxicity of single cells using arrays of microwells, the method comprising steps of:
    monitoring lysis of target cells in microwells that contain a single effector cell and at least one target cell; and
    simultaneously profiling activation markers or secreted soluble mediators,
    wherein the monitoring comprises a step of detecting lysis of said target cells by said single effector cell using a fluorescent indicator; and
    wherein the profiling comprises a step of contacting the microwells with a substrate, wherein a surface of the substrate contains thereon agents that bind to said activation markers or secreted soluble mediators.

2. The method of claim 1, wherein the monitoring step comprises:
    culturing the at least one target cell and the single effector cell under conditions conducive to lysis of the target cell by the effector cell.

3. The method of claim 2, further comprising a step of:
    recovering the single effector cell from at least one of the microwells.

4. The method of claim 2, wherein the monitoring comprises detecting loss of target cell fluorescence over time.

5. The method of claim 3, further comprising culturing the recovered single effector cell to obtain a clonal amplification of the recovered single effector cell.

6. The method of claim 3, further comprising characterizing sequence or expression of one or more genes in the recovered single effector cell.

7. The method of claim 1, wherein the single effector cell and the target cells are human cells.

8. The method of claim 1, wherein said profiling further comprises a step of
    determining on the surface of the substrate the locations of agent binding to said activation markers or secreted soluble mediators.

9. The method of claim 1, wherein the single effector cell is a cytotoxic T lymphocyte (CTL).

10. The method of claim 1, wherein the activation markers or secreted soluble mediators comprise one or more cytokines.

11. The method of claim 1, 2, 3, or 8 wherein the target cells are HIV-infected cells.

12. The method of claim 1, wherein the depth of the microwells is less than 100 µM.

13. The method of claim 1, wherein dyes are used to label both the target cells and the single effector cell.

14. The method of claim 1, further comprising using software to recognize where killing took place and to locate those microwells for a micromanipulator.

15. The method of claim 1, 2, or 9, wherein secreted soluble mediators are simultaneously profiled.

16. The method of claim 11, wherein secreted soluble mediators are simultaneously profiled.

17. The method of claim 9, wherein the activation markers or secreted soluble mediators comprise one or more cytokines.

18. The method of claim 1, wherein the microwells containing the target cells and single effector cells are held in physical contact with said substrate, and wherein said substrate is a glass slide pre-functionalized with said agents to capture the activation markers or secreted soluble mediators.

19. The method of claim 15, wherein the microwells containing the target cells and single effector cells are held in physical contact with said substrate, and wherein said substrate is a glass slide pre-functionalized with said agents to capture the activation markers or secreted soluble mediators.

* * * * *